United States Patent [19]
Schinkel et al.

[11] Patent Number: 5,167,222
[45] Date of Patent: Dec. 1, 1992

[54] INSTRUMENT SET FOR OPERATING ON THE UTERUS

[75] Inventors: Otto Schinkel, Bovenden; Josef Horvath, Göttingen, both of Fed. Rep. of Germany

[73] Assignee: Labotect-Labor-Technik, Gottingen, GmbH, Bovenden, Fed. Rep. of Germany

[21] Appl. No.: 613,398

[22] Filed: Nov. 15, 1990

[30] Foreign Application Priority Data

Dec. 4, 1989 [DE] Fed. Rep. of Germany ....... 3940064

[51] Int. Cl.$^5$ ............................................. A61B 1/32
[52] U.S. Cl. ............................................. 128/17
[58] Field of Search ............................ 128/17, 18, 19

[56] References Cited

U.S. PATENT DOCUMENTS

| | | | |
|---|---|---|---|
| 2,545,201 | 3/1951 | Gilbert | 128/17 |
| 2,844,144 | 7/1958 | Massey | 128/17 |
| 2,858,826 | 11/1958 | Kahn | 128/17 |
| 3,320,948 | 5/1967 | Martin | 128/17 |
| 3,789,829 | 2/1974 | Hasson | 128/17 X |
| 3,847,143 | 11/1974 | Cotey et al. | 128/17 |
| 4,085,756 | 4/1978 | Weaver | 128/17 X |
| 4,323,057 | 4/1982 | Jamieson | 128/17 |
| 4,350,151 | 9/1982 | Scott | 128/17 |
| 4,432,352 | 2/1984 | Wineland | 128/17 |

*Primary Examiner*—John G. Weiss
*Assistant Examiner*—Nicholas D. Lucchesi
*Attorney, Agent, or Firm*—Hopkins & Thomas

[57] ABSTRACT

An instrument set for operating on the uterus (1) comprising a speculum (5) with an upper spoon (7) and a swivelling lower spoon (8) attached to the upper spoon by a stretching device. A ball forceps (20) is provided for grasping the portio (2). In the upper and lower spoon (7,8) of the speculum recesses (16,17) are provided which ensure the rigid seat of the speculum (5) in the vagina (6). On the speculum (5) an abutment (19) is provided and on the ball forceps (20) a corresponding extension (30, 31) is provided for hooking in the ball forceps (20).

19 Claims, 2 Drawing Sheets

INSTRUMENT SET FOR OPERATING ON THE UTERUS

FIELD OF THE INVENTION

The present invention relates to an instrument set for operating on the uterus comprising a speculum with an upper spoon and a swivellably mounted lower spoon attached to it by a stretching means, and a ball forceps for grasping the portio. The present instrument set facilitates the performance of operations on the uterus. The instrument set may furthermore be used for transvaginal gamete transfers and for tubal catheterisation.

BACKGROUND OF THE INVENTION

An instrument set of the above mentioned kind is known in which more or less pipe-shaped upper and lower spoons comprise a smooth surface. The upper spoon is at its rear end nearly precisely pipe-like. The lower spoons is swivellably mounted in the lateral cheeks. The two spoons are extended in their far ends to form stretching levers which belong to a stretching means. Such stretching means furthermore comprises a screw and a nut. This stretching means enables the upper and lower spoon to be moved apart after insertion into the vagina and the respective turning movement, so that the doctor may view the portio from above. This known instrument set comprises a ball forceps which allows grasping the portio and pulling the uterus forward. The ball forceps comprises handle ends extending straight backwards from the joint and has on its front end articulated lever ends. The disadvantage of this instrument set lies in the fact that due to the even surface of the spoons, the danger arises that the speculum slips out of the vagina if it is not permanently held. Furthermore, after having grasped the portio, the ball forceps also has to be held. Thus, for the purpose of holding the speculum and the ball forceps, two hands are required and the doctor consequently needs somebody to help him, as otherwise he would not have a free hand to perform the operation.

For the transvaginal gamete transfer the instrument set is completed by a plastic catheter which is inserted into the uterus along the endometrium. The disadvantage here lies in the fact that grooves come about and injuries in the endometrium occur.

SUMMARY OF THE INVENTION

It is an object of the present invention to further develop an instrument set of the above kind in such a manner that the speculum and the ball forceps can be applied without having to permanently use two hands. The doctor is to have his hands free for performing the operation. In a further arrangement of the present invention, the instrument set is to improve the transvaginal gamete transfer and the tubal catheterisation.

DETAILED DESCRIPTION

According to the invention this is achieved in that in the upper and lower spoons, recesses are provided which ensure the rigid seat of the speculum in the vagina, and that on the speculum an abutment is provided and that on the ball forceps a corresponding extension is provided for hooking in the ball forceps. Due to the recesses in the upper and lower spoon, the muscular vaginal wall partially enters the recesses after inserting the speculum and moving it apart by the stretching means, thus achieving a rigid seat and preventing the speculum from slipping out of the vagina due to pressing movements. The abutment on the speculum enables a corresponding extension on the ball forceps to be accepted after the ball forceps has grasped the portio and brought the uterus into a more or less stretched position. After the ball forceps has been hooked into the speculum's abutment by its extension, these components of the instrument set are in their proper relative position. They need not be held by hand and the doctor has both hands free to perform the operation. The upper spoon is usually arranged on its front end slightly shorter than the lower spoon, thus enabling the uterus to be brought into a more preferable position.

The upper spoon may preferably comprise on its rear end a deep recess for improving the direct view on the portio. This deep recess is made up to the upper spoon's cheeks and extends up to ¼ of the upper spoon's length.

In the area between its joint and the free handle ends of the joint arms, the ball forceps may be articulated. This articulation is approx. 45°, so that the free handle ends may be moved out of the surgeon's working area.

The extension on the ball forceps is provided beneath the joint and comprises a guide plate which is penetrated on both sides by a protruding bolt. The abutment on the speculum comprises two guiding walls which are arranged at the distance of the guiding plate and comprise notches. This is a particularly preferable arrangement as the ball forceps is not only held by its being hooked in, but, simultaneously, also guided and secured against turning. Naturally, other arrangements are also possible.

The instrument set may additionally comprise a catheter guiding tube which is, in its front end section, flexible and spirally rolled and which is arranged, in its front end, spherically. This catheter guiding tube belongs to the instrument set as a new component. It is spirally rolled at least in its front section and thus comprises a very large flexibility which allows it to easily adapt to curvatures and, consequently, avoids grooves in and injuries to the endometrium. The spherical end is particulary effective in achieving this target. The catheter guiding tube is provided for taking in and guiding the catheter which, up to the present day, was used without this guiding tube.

Preferably, the ball forceps may comprise on its side showing away from the extension a clamping device having spring mounted clamping jaws for grasping the catheter guiding tube. This allows fixing the catheter guiding tube in the ball forceps' clamping device, whereby the ball forceps is hooked into the speculum. Thus, after insertion, the catheter guiding tube is rigidly attached in its rear end section, so that it not longer needs to be held while inserting the catheter.

The catheter guiding tube may comprise in its rear end section a radially displaced wing and be arranged arcuated in its front end section with regard to its axis, whereby the wing moves to a position on the catheter guiding tube according to the arcuation. Thus the doctor may observe and follow on the rear end the forward arcuation of the catheter guiding tube, so that specific turning of the front end of the catheter guiding tube is enabled.

The catheter guiding tube may comprise, on its outer side, a scale for orientation purposes which, for example, cooperates with the clamping device, in order to allow the doctor during multiple use of the instrument set in one and the same patient, to introduce the catheter guiding tube for a further use in such a manner that its front end keeps its proper place and is not introduced too deeply.

The catheter guiding tube is accompanied by a catheter. The catheter's front end section has a reduced diameter, so that the isthmian tube section can be reached with little resistance. In this section the catheter protrudes from the catheter guiding tube and is applied without the guiding tube.

The catheter may comprise on its outer side a scale cooperating with the rear end of the catheter guiding tube, thus showing how far the front end of the catheter has protruded from the front end of the catheter guiding tube.

The invention may be carried into practice in various ways and a preferable embodiment will now be described by way of example with reference to the accompanying drawings in which.

Figure 1:
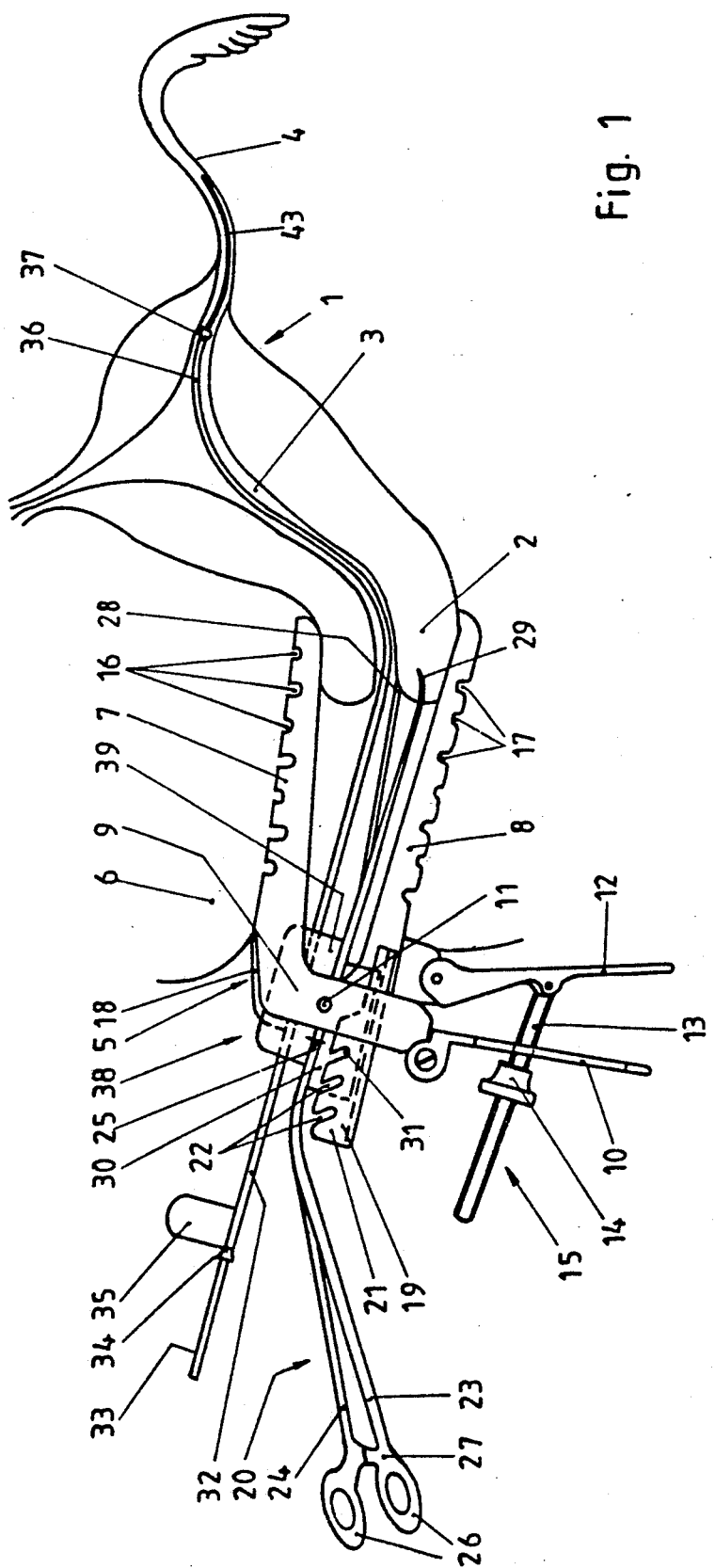
FIG. 1 is a partial sectional view of the essential parts of the instrument set in a position during use.
Figure 2:
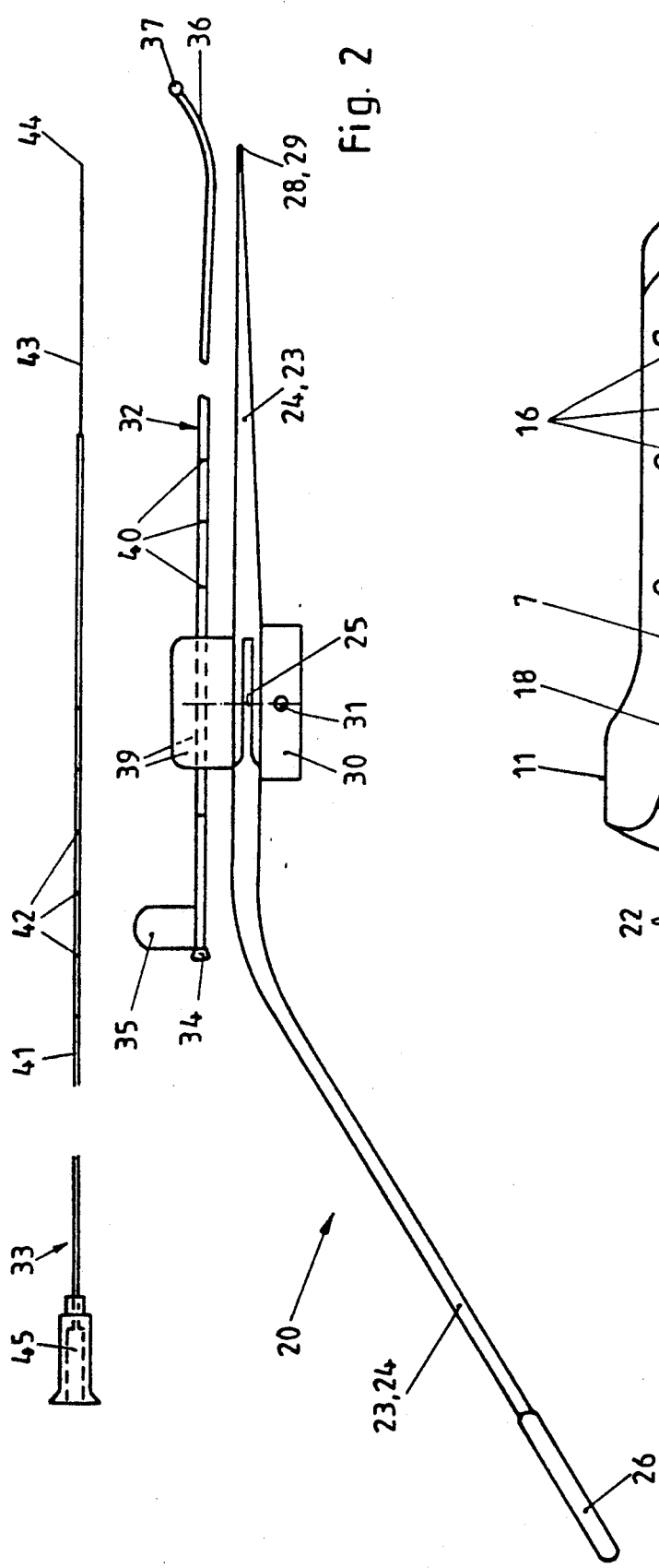
FIG. 2 is a view of parts of the instrument set in individual display.
Figure 3:
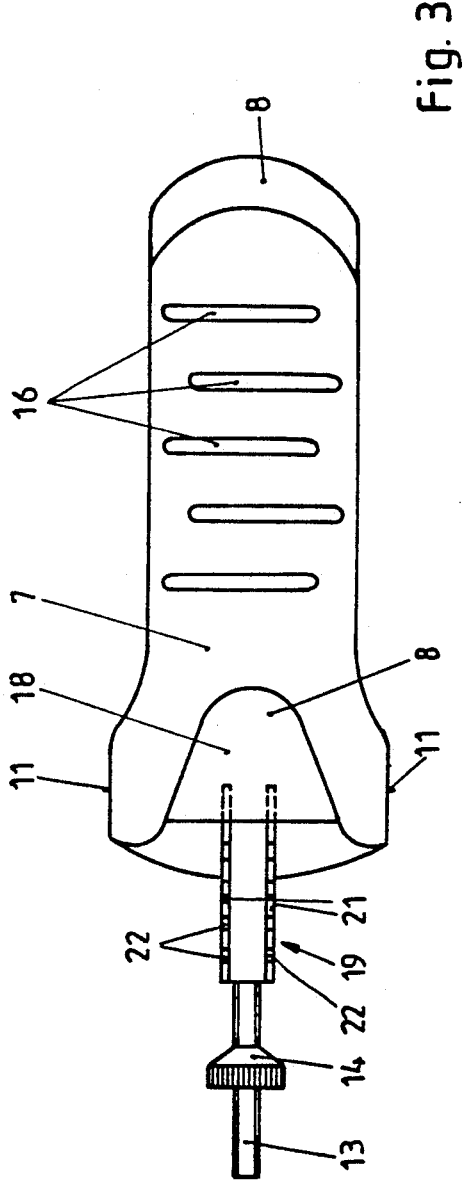
FIG. 3 is a top view of the speculum.

A uterus 1 is schematically displayed in FIG. 1 with portio 2, endometrium 3 and a tube 4. A speculum 5 has been inserted into the vagina 6. Speculum 5 comprises an upper spoon 7 and a lower spoon 8. Upper spoon 7 is arranged in its rear end nearly pipe-like due to cheeks 9. Stretching lever 10 acts in the front part at the lower end. Upper spoon 7 comprises in the mid-section of the cheeks 9 a joint 11 by means of which lower spoon 8 is mounted swivellably in its rear section to upper spoon 7. Lower spoon 8 extends into stretching lever 12. Screw 13 is coupled with it by means of a joint and protrudes through a recess in in stretching lever 10. Screw 13 is accompanied by a nut 14, so that by turning nut 14, which then sits close to stretching lever 10, a stretching means 15 is brought about by which, through relative turning of nut 14, upper spoon 7 and lower spoon 8 of speculum 5 may be moved apart from one another or moved together. The speculum 5 is shown in FIG. 1 in the desired stretched position. It is inserted into the vagina in a closed position, turned 90°, and then moved apart by using stretching means 15. Upper spoon 7 comprises recesses 16 and lower spoon 8 recesses 17. These recesses 16, 17 have a closed edge, are shaped like oblong slits, and are arranged in an off-set manner from one another along the length of each spoon remote from the front end of each spoon (FIG. 3). Recesses 16 and 17 may also have other shapes, e.g. they may be elongated or round. Upon stretching the speculum 5, the wall 6 of the vagina partially moves into recesses 16 and 17, whereupon the speculum achieves a rigid and immovable seat. Upper spoon 7 comprises in its rear end a recess 18 having an open edge (FIG. 3), which considerably improves the doctor's view on the portio 2.

On speculum 5, in particular on lower spoon 8, an abutment 19 is arranged and provided for a ball forceps 20. The abutment may comprise a U-shaped cross section, in such a manner two guiding walls 21 are formed. Such guiding walls are arranged parallel and at a distance to each other. They comprise notches 22 which have an open edge and are, as can be seen in FIG. 1, arranged obliquely.

Ball forceps 20 comprises two articulated arms 23 and 24 which are connected to each other via joint 25 like a pair of scissors. On the rear end of articulated arms 23 and 24 there are handles 26. Between these a locking bridge 27 is arranged, as is well known in other medical instruments. The articulated arms 23 and 24 are articulated in the area approximately between joint 25 and the handles 26, whereby the articulation is approx. 45° downwards. The front ends of articulated arms 23 and 24 comprise the two inwardly bent sections 28 and 29 by means of which the portio 2 may be grasped and held.

Furthermore, ball forceps 20 comprises a guiding plate 30 approximately below the area in which joint 25 is arranged, which, for example, is screwed under articulated arm 24. This guiding plate 30 has a smaller thickness than the distance between the guiding walls 21 of abutment 19, so that the ball forceps may be guidedly inserted into abutment 19. Guiding plate 30 is penetrated by a bolt 31 which protrudes at a certain distance from the guiding plate 30 to the left and the right, the distance being such-like as to allow effective connection with notches 22 in guiding walls 21.

Such an instrument set is handled as follows: At first speculum 5 is brought into a closed position, i.e. to create a position by turning nut 14 relative to screw 13 in which upper spoon 7 and lower spoon 8 are very close to each other or even touch each other. In this position speculum 5 is inserted into the vagina 6 and turned approx. 90°. Then the stretching is performed by stretching means 15, whereupon via joint 11 upper spoon 7 and lower spoon 8 move apart from one another until speculum 5 achieves a rigid and immovable seat in vagina 6. Subsequently portio 2 is grasped by ball forceps 20 and uterus 1 is brought into a stretched position by pulling ball forceps 20. In this position ball forceps 20 is hooked into notch 22 of abutment 19 by means of bolt 31, so that the doctor's hands are free to perform the operation. Recess 18 in upper spoon 7 allows a more or less free view on portio 2.

For the purpose of a transvaginal gamete transfer and tubal catheterisation, the instrument set is accompanied by a catheter guiding tube 32 and a catheter 33. The catheter guiding tube 32 comprises in its rear end an insertion cone 34 for catheter 33. In this end section a radially displaced wing 35 is provided which is arranged such-like as to coincide with the predefined curvature 36 in the front end section of catheter guiding tube 32. Directly on the front end of the catheter guiding tube 32 a sphere 37 is provided. The sphere's roundness facilitates the introduction of catheter guiding tube 32. Naturally, the catheter guiding tube 32 is hollow and allows insertion of catheter 33. The catheter guiding tube 32 is very flexible, particularly in its front end section up to approximately half of the overall length, and consists of rolled ribbon, thus allowing this amount of flexibility.

Whereas below joint 25 of ball forceps 20 the guiding plate 30 is provided, above joint 25 is provided a clamping device 38 consisting of spring mounted clamping jaws pressing against each other, whereby between the two clamping jaws 39 a clamping gap is formed, such gap being adjusted in its arrangement and size for accepting the catheter guiding pipe 32, so that after insertion of the catheter guiding pipe 32, the pipe is clamped between clamping jaws 39 of clamping device 38, thus achieving a rigid seat for the tube and, finally, mounting it via ball forceps 20 on speculum 5. The catheter guiding tube 32 is properly seated when sphere 37 is located at the entrance of tube 4. On the outside of catheter guiding tube 32 a scale 40 is attached which cooperates with clamping jaws 39 and serves for orientation purposes.

Catheter 33 consists, more or less, of a thin plastic tube 41 and is arranged very flexibly. Furthermore, it comprises on the outside a scale 42 which cooperates with the end of catheter guiding tube 32, i.e. insertion cone 34. The plastic tube comprises a front end section 43 which has a reduced diameter with regard to the other part of plastic tube 41. This is the part of catheter 33 which is pushed beyond the front end of catheter guiding tube 32 in order to reach the isthmian tube section. The front end 44 of catheter 33 is rounded off. The rear end of catheter 33 comprises a connection piece 45 for connecting a syringe.

The use of the instrument set consisting of speculum 5, ball forceps 20, catheter guiding tube 32 and catheter 33 takes place as follows:

At first speculum 5 and ball forceps 20 are handled as is described above. Then the insertion of the catheter guiding tube 32 takes place via the endometrium 3 up to the entrance of tube 4. The catheter guiding tube 32 may then be inserted very sensitively. By turning catheter guiding tube 32 the curvature 36 may be displaced in such a manner that the insertion takes place by the lowest possible resistance and without any injuries whatsoever. Wing 35 shows the surgeon to which side the curvature is directed. As soon as the catheter guiding tube 32 has reached its proper position, it is clamped into clamping device 38, whereby the surgeon is given the possibility to write down the proper position and the insertion depth by viewing scale 40, which facilitates two or more applications of the instrument set in one and the same patient. After the catheter guiding tube 32 has been clamped in the clamping device 38 by means of clamping jaws 39 and is thus tightly held, the surgeon has both hands free to handle catheter 33. The catheter is inserted by its front end 44 into the insertion cone 34. Such insertion is only performed until the front end 44 lies close to sphere 37. This is indicated to the surgeon by the beginning of scale 42, the first line of which is located at the insertion cone 34. Every further line of scale 42, the distance between which may be, for example, a centimetre, indicates how far the front end 44 or the end section 43 has emerged from the catheter guiding tube 32 and has exceeded sphere 37 when continuing to insert catheter 33. Catheter 33 is also inserted sensitively until end section 43 penetrates the isthmian tubal section. The surgeon may now write down this position which is specific for this patient by using scale 42. This allows performing the transvaginal gamete transfer.

List of References

1 = Uterus
2 = Portio
3 = Endometrium
4 = Tube
5 = Speculum
6 = Vagina
7 = Upper spoon
8 = Lower spoon
9 = Cheek
10 = Stretching lever
11 = Joint
12 = Stretching lever
13 = Screw
14 = Nut
15 = Stretching means
16 = Recesses
17 = Recesses
18 = Recess
19 = Abutment
20 = Ball forceps
21 = Guiding wall
22 = Notch
23 = Articulated arm
24 = Articulated arm
25 = Joint
26 = Handle
27 = Locking bridge
28 = Bend
29 = Bend
30 = Guiding plate
31 = Bolt
32 = Catheter guiding tube
33 = Catheter
34 = Insertion cone
35 = Wing
36 = Curvature
37 = Sphere
38 = Clamping device
39 = Clamping jaw
40 = Scale
41 = Plastic tube
42 = Scale
43 = End section
44 = End
45 = Connection

We claim:

1. An instrument set for operating on the uterus comprising
    a speculum having an upper spoon, a swivelling lower spoon attached to said upper spoon, and stretching means for moving apart said upper and lower spoons each of said spoons having a front end opposite the end at which said spoons are attached and a rear end;
    a ball forceps for grasping the portio;
    said upper and lower spoons each having spaced recesses along their length and remote from said front end, for seating said speculum within a vaginal cavity; and
    said speculum being provided with an abutment and said ball forceps being provided with a corresponding extension for engaging said abutment and maintaining said ball forceps in a selected position.

2. An instrument set as claimed in claim 1, wherein said rear end of said upper spoon includes a deep recess for extending an open view of the portio and said spaced recesses in said upper and lower spoons are formed at an angle from the direction of insertion of said spoons into the vaginal cavity.

3. An instrument set as claimed in claim 1, wherein said ball forceps comprises two articulated arms connected at a joint and free handles at adjacent ends of said arms, said arms forming a knee in the area between said joint and said free handles.

4. An instrument set as claimed in claim 1, wherein said extension on said ball forceps comprises a guiding plate, and further comprises a bolt penetrating said guide plate, and wherein said abutment on said speculum comprises two guiding walls having notches, said guiding walls being spaced a distance equivalent to the width of said guiding plate.

5. An instrument set as claimed in claim 1 further comprising a catheter guiding tube having a spirally rolled flexible front end section, a rear end section, and a spherical front end for facilitating insertion of said tube.

6. An instrument set as claimed in claim 5, wherein said ball forceps is provided on its side opposite said extension a clamping device having spring mounted clamping jaws for grasping said catheter guiding tube.

7. An instrument set as claimed in claim 5, wherein said catheter guiding tube comprises at its rear end section a radially extending wing and, at its front end section, is arcuated with regard to its axis, whereby said wing moves to a position on said catheter guiding tube according to the arc of said front end section.

8. An instrument set as claimed in claim 5, wherein said catheter guiding tube comprises on its exterior side a scale for orientation purposes.

9. An instrument set as claimed in claim 5, further comprising a catheter having a front end section of reduced diameter, said catheter adapted to move within said catheter guiding tube.

10. An instrument set as claimed in claim 9, wherein said catheter is provided with an exterior side scale for cooperation with said catheter guiding tube scale.

11. An instrument set as claimed in claim 1, wherein said abutment and said corresponding extension are positioned with respect to said upper and lower spoons to secure said ball forceps to said speculum in a manner allowing said ball forceps to extend between said upper and lower spoons and toward the uterus.

12. An instrument set as claimed in claim 1, wherein said recesses provided along the length of said upper and lower spoons are provided along the exterior faces of said spoons and are of sufficient size to cause the wall of the vaginal cavity to move partially into said recesses for securing said spoons.

13. An instrument set for operating on the uterus comprising a speculum having an upper spoon, a swivelling lower spoon attached to said upper spoon, and stretching means for moving apart said upper and lower spoons;
a ball forceps for grasping the portio;
said upper and lower spoons each having recesses along their length for seating said speculum within a vaginal cavity;
said speculum being provided with an abutment and said ball forceps being provided with a corresponding extension for engaging said abutment;
said extension comprising a guiding plate with a bolt penetrating said plate and in which said abutment comprises two guiding walls having notches formed therein, said walls being spaced a distance equivalent to the width of said plate.

14. An instrument set as claimed in claim 13 further comprising a catheter guiding tube having a spirally rolled flexible front end section, a rear end section, and a spherical front end for facilitating insertion of said tube.

15. An instrument set as claimed in claim 13, wherein said ball forceps is provided on its side opposite said extension a clamping device having spring mounted clamping jaws for grasping said catheter guiding tube.

16. An instrument set as claimed in claim 13, wherein said catheter guiding tube comprises at its rear end section a radially extending wing and, at its front end section, is arcuated with regard to its axis, whereby said wing moves to a position on said catheter guiding tube according to the arc of said front end section.

17. An instrument set as claimed in claim 13, wherein said catheter guiding tube comprises on its exterior side a scale for orientation purposes.

18. An instrument set as claimed in claim 13, further comprising a catheter having a front end section of reduced diameter, said catheter adapted to move within said catheter guiding tube.

19. An instrument set as claimed in claim 13, wherein said catheter is provided with an exterior side scale for cooperation with said catheter guiding tube scale.

* * * * *